United States Patent [19]

Fujiwara et al.

[11] Patent Number: 5,106,163
[45] Date of Patent: Apr. 21, 1992

[54] METHOD AND APPARATUS FOR INSPECTING A FORWARD END PORTION IN A TUNNELING MACHINE

[75] Inventors: Toshio Fujiwara, Asaka; Yukio Yamashita, Kiyose, both of Japan

[73] Assignee: Obayashi Corporation, Osaka, Japan

[21] Appl. No.: 596,725

[22] Filed: Oct. 10, 1990

[30] Foreign Application Priority Data

| Oct. 17, 1989 | [JP] | Japan | 1-267989 |
| Oct. 20, 1989 | [JP] | Japan | 1-271641 |
| Aug. 31, 1990 | [JP] | Japan | 2-227942 |

[51] Int. Cl.$^5$ .......................... F21C 35/22; F21D 9/06
[52] U.S. Cl. .......................... 299/1.3; 175/40; 299/33; 299/81; 405/144
[58] Field of Search .............. 299/1, 30, 33, 56, 81; 175/39, 40, 49; 405/138, 144

[56] References Cited

U.S. PATENT DOCUMENTS

| 1,353,908 | 9/1920 | Hodgson | 299/81 X |
| 3,379,024 | 4/1968 | Wohlmeyer | 299/33 X |
| 3,830,549 | 8/1974 | Sugden | 299/33 |
| 4,368,924 | 1/1983 | Nussbaumer | 405/144 X |

FOREIGN PATENT DOCUMENTS

| 60-144607 | 7/1985 | Japan . |
| 1153059 | 4/1985 | U.S.S.R. | 299/30 |

Primary Examiner—David J. Bagnell
Attorney, Agent, or Firm—Wenderoth, Lind & Ponack

[57] ABSTRACT

A system for inspecting a forward end portion in a tunneling machine including cutter bits and a chamber such as a tunnel boring machine or a shield tunneling machine. The system includes an apparatus for inspecting a forward end portion comprising at least one through hole provided on the partition wall for defining a chamber, an elongate member slidably and rotatably inserted into the through hole, an image sensor positioned at a forward end of the elongate member for observing a cutter bit or the inside of the chamber, an image display provided in the main body for displaying an image from the image sensor, and a connection for connecting the image sensor and the image display. The system also includes a method for inspecting a forward end portion comprising the steps of defining a cavity in the chamber or in the vicinity of the cutter bits by supplying compressed air, inserting an image sensor into the cavity, and observing the inside of the chamber or the cutter bits using the image sensor.

18 Claims, 10 Drawing Sheets

METHOD AND APPARATUS FOR INSPECTING A FORWARD END PORTION IN A TUNNELING MACHINE

BACKGROUND OF THE INVENTION

The present invention relates to a system for inspecting a forward end portion in a tunneling machine, and more particularly, to a system for inspecting a forward end in a tunneling machine such as a tunnel boring machine or a shield tunneling machine in which the wear of cutter bit or the properties of the ground or the like can be observed without discontinuing the tunneling work or removing the excavated soil.

Conventionally, a tunnel boring machine has been known as a tunneling machine which is employed to construct a tunnel in relatively solid ground.

Figure 1:
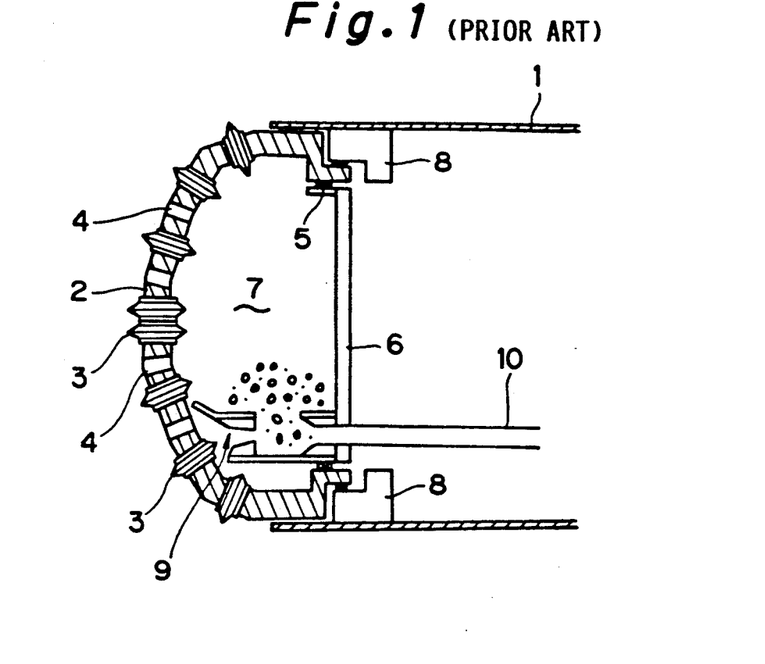
FIG. 1 is a schematic cross-sectional view showing a conventional tunnel boring machine.

In FIG. 1, this type of tunnel boring machine is shown. The tunnel boring machine includes a cylindrical main body 1 having both side ends open and a cutter plate 2 provided on an open forward end of the main body 1 having a hemispherical shape. On the cutter plate 2 are provided a plurality of roller-cutters 3 which are rotatably supported thereon and openings 4 for introducing the excavating soil between the roller-cutters 3. A disk-shaped partition wall 6 is provided inside the cutter plate 2 in a state where a sealing material 5 is interposed between the partition wall 6 and the inner periphery of the cutter plate 2, thereby defining a chamber 7 for accommodating the excavated soil at the rear of the cutter plate 2.

A motor 8 is provided adjacent to the outer periphery of the cutter plate 2 so that the cutter plate 2 is connected to the motor 8 through gears.

At the lower portion of the chamber 7, there is provided a nozzle 9 to which high-pressure water is supplied from a device provided at the rear of the main body 1. A discharge pipe 10 pierces through the partition wall 6 and is disposed in confrontation with the nozzle 9.

In the tunnel boring machine thus constructed, the cutter plate 2 is rotated by the motor 8 while thrusting the main body 1 forward by a propelling jack (not shown), thereby excavating the ground with the roller-cutters 3.

The excavated soil is introduced into the chamber 7 from the openings 4 and mixed with the water ejected from the nozzle 9 to form a slurry, and the soil in the form of a slurry is discharge to the outside through the discharge pipe 10.

By repeating the above operations, a tunnel is constructed by the tunnel boring machine. However, this type of tunneling machine is employed when excavating relatively solid ground, so that the roller-cutters are worn away in a short time. Therefore, in order to maintain the efficiency of excavation, the degree of wear on the roller-cutters must be known.

Although the properties of the ground to be excavated is investigated in advance, it is not grasped in detail, and therefore the state of ground and the excavated soil must be directly observed by one's eyes.

Thus, conventionally, a worker enters into the chamber 7 to inspect the state of wear in the roller-cutter 3 and the properties of the ground. However, such a method of inspecting has the following disadvantages.

That is, in the above inspection, since a worker enters into the chamber 7, the excavating operation must be discontinued, thus decreasing the efficiency of the excavation.

Further, in this type of tunnel boring machine, since the chamber 7 is not pressurized, as opposed to a shield tunneling machine, it is easier for a worker to enter into the chamber 7 as compared with the shield tunneling machine. However, since the excavated soil is accommodated in the chamber 7, the worker cannot enter into the chamber 7 unless the soil is removed therefrom. This removal of soil is troublesome work, due to the limited space inside the chamber.

On the other hand, in the shield tunneling machine, such as an earth pressure balance type or a slurry type of shield tunneling machine, excavation of a tunnel cannot be performed sometimes during shield tunneling, for some reason or other. This failure of excavation is caused by various reasons, including adhesion of soil to the chamber, obstructions in front of the cutter, wear or breakdown of the cutter bit, or the occurrence of cavities due to ground settlement.

In case of the occurrence of the above malfunctions, since the chamber in front of the partition wall is filled with muddy water or mud, and thus pressurized, the state inside the chamber cannot be easily observed.

Further, the cutter face not only cannot be observed by one's eyes, but wear or breakdown of the cutter bit cannot be directly inspected.

As a means for detecting the wear or breakdown of the cutter bit, there is a known wear detecting device using ultrasonic waves, for example, disclosed in Japanese Laid-Open Publication No. 60-144607. However, in this wear detecting device, wear of a detecting bit juxtaposed with cutter bits is detected, thereby estimating the wear degree of the other cutter bits. That is, the wear of a cutter bit is estimated from a detecting bit and as a result, the wear of the cutter bit cannot be accurately detected.

SUMMARY OF THE INVENTION

It is therefore an object of the present invention to provide a system for inspecting a forward end portion in a tunneling machine in which the wear of a cutter bit or the properties of the ground can be observed without discontinuing the tunneling work or removing the excavated soil.

Another object of the present invention is to provide a system for inspecting a forward end portion in a tunneling machine in which a pressurized forward end portion of a shield tunneling machine can be inspected by an image sensor.

In order to achieve the above objects, according to one aspect of the present invention, there is provided an apparatus for inspecting a forward end portion in a tunneling machine including a main body, a cutter member rotatably provided at a forward end portion of the main body and having a plurality of cutter bits and openings thereon, and a partition wall provided at the inside of the cutter member to define a chamber between the cutter member and the partition wall. The apparatus comprises at least one through hole provided on the partition wall. An elongate member is inserted into the through hole, the elongate member being slidable in a front-rear direction and rotatable around its longitudinal axis. An image sensor is positioned at a forward end of the elongate member. An image displaying means is provided in the main body for displaying an image from the image sensor, and a connecting means connects the image sensor and the image displaying means, the connecting means extending in the elongate member.

With the above structure, the image sensor can be positioned inside of the chamber or in the vicinity of the cutter bits or in confrontation with the ground by moving the elongate member in a front-rear direction and rotating the same. An image signal from the image sensor is transmitted to the image displaying means through the connecting means, thereby displaying an image of the inside of the chamber or the cutter bits or the ground on the image displaying means.

According to another aspect of the present invention, there is provided an apparatus for washing a forward end portion in a tunneling machine including a cutter member rotatably provided at a forward end portion of a main body and having a plurality of cutter bits and openings thereon, with a partition wall provided inside of the cutter member to define a chamber between the cutter member and the partition wall. The apparatus comprises at least one through hole provided on the partition wall. An elongate member is inserted into the through hole, the elongate member being slidable in a front-rear direction and rotatable around its longitudinal axis. A nozzle is provided at a forward end of the elongate member and is rotatable around and axis approximately perpendicular to the longitudinal axis of the elongate member. A rotating mechanism is provided on or in the elongate member for rotating the nozzle, and a water supply tube provided in the elongate member supplies water to the nozzle.

With the above structure, the inside of the chamber or the cutter bits can be washed while moving the elongate member in a front-rear direction and rotating the same around its longitudinal axis and rotating the nozzle around an axis approximately perpendicular to the longitudinal axis of the elongate member before observation and inspection is performed by the apparatus for inspecting a forward end portion. Therefore, the inside of the chamber or the cutter bit can be exactly observed and inspected by the above inspecting apparatus.

According to still another aspect of the present invention, there is provided a method for inspecting a forward end portion in a tunneling machine including a main body, a cutter member rotatably provided at a forward end portion of the main body having a plurality of cutter bits and openings thereon, and a partition wall provided at inside of the cutter member to define a chamber between the cutter member and the partition wall. The method comprises the steps of defining a cavity in the chamber or in the vicinity of the cutter bits by supplying compressed air, inserting an image sensor into the cavity, the image sensor piercing through the partition wall and sealed in watertight or airtight, and observing the inside of the chamber or the cutter bits using the image sensor.

With the above method, upon supplying compressed air to the inside of the chamber or the cutter face, the level of muddy water, mud or the excavated soil is lowered up to a certain height while maintaining the stability of the cutter face, thereby defining a cavity. As a result, observations can be freely performed in the cavity by the image sensor without being affected by the excavated soil.

The above and other objects, features and advantages of the present invention will become more apparent from the following description when taken in conjunction with the accompanying drawings in which preferred embodiments of the present invention are shown by way of illustrative examples.

BRIEF DESCRIPTION OF THE DRAWINGS

In the drawings:

FIGS. 3(A) and (B) are, respectively, cross-sectional top and side views showing a swing mechanism in the apparatus for inspecting a forward end portion in a tunneling machine according to the first embodiment of the present invention;

DETAILED DESCRIPTION OF THE INVENTION

A system for inspecting a forward end portion in a tunneling machine will be described below with reference to FIGS. 2 through 12.

Figure 2:
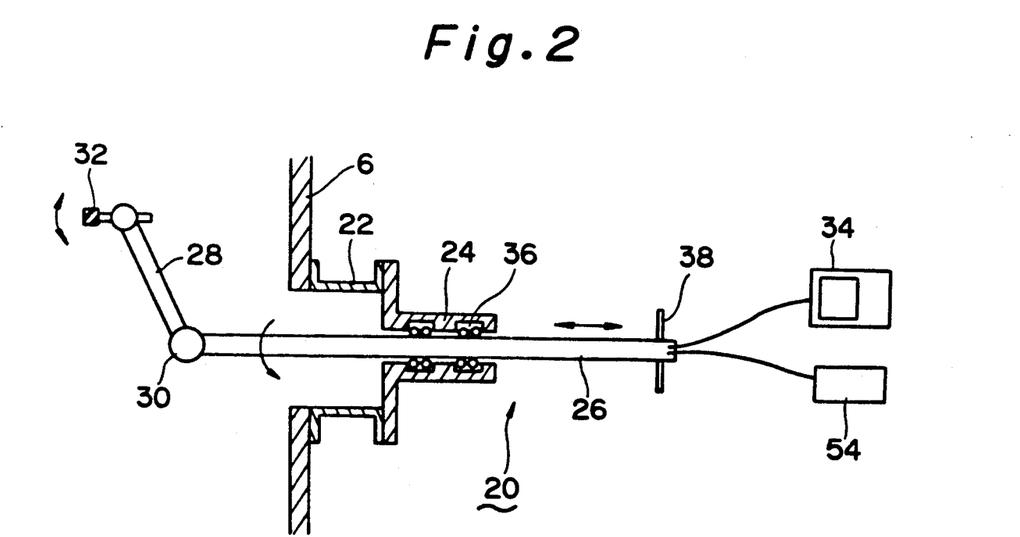
FIG. 2 is a cross-sectional view showing an apparatus for inspecting a forward end portion in a tunneling machine according to a first embodiment of the present invention.
Figure 3:
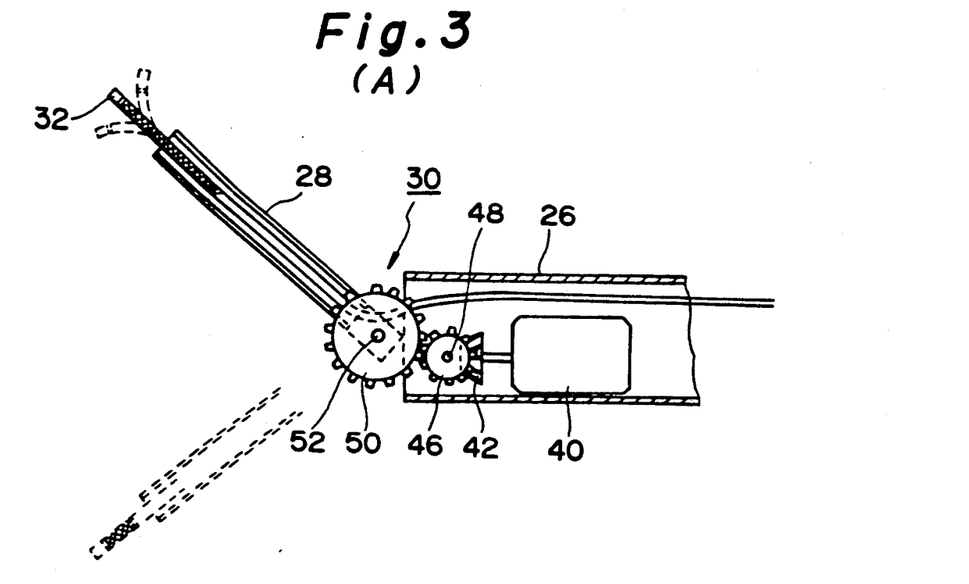

FIGS. 2 and 3 show a first embodiment of an apparatus for inspecting a forward end portion in a tunneling machine according to the present invention.

An apparatus for inspecting a forward end portion (hereinafter referred to as an inspecting apparatus) in FIGS. 2 and 3 is applied to the tunnel boring machine in FIG. 1. The tunnel boring machine has the same structure as a conventional machine of this type.

The inspecting apparatus 20 is attached to an attachment flange 22 fixed to the partition wall 6 and disposed around a hole bored, in place, through the partition wall 6 when inspection is carried out. A plurality of attachment flanges 22 are disposed, for example, on concentric circles at suitable intervals from the center of the partition wall 6. These attachment flanges 22 are closed by a blanking cover while inspection is not performed.

The inspecting apparatus 20 includes a guide pipe 24 connected tightly to the attachment flange 22, a slide pipe 26 inserted into the guide pipe 24 and an arm 28 swingably provided at the tip end of the slide pipe 26. The inspecting apparatus 20 further includes a swing mechanism 30 interposed between the slide pipe 26 and the arm 28, an image sensor 32 supported at the tip end of the arm 28 and an image display device 34 connected to the image sensor 32.

The slide pipe 26 has a hollow cylindrical shape with both ends open. The slide pipe 26 is disposed in the guide pipe 24 through bearings 36 so that the slide pipe 26 is movable in a front-rear direction and rotatable with respect to the guide pipe 24. The slide pipe 26 has an operation handle 38 attached thereto at the rear side thereof.

The image sensor 32 comprises a portable camera using a charge coupled device (CCD), or a fiber scope using an optical fiber, or an optical mirror, and the image sensor 32 is connected to the image display device 34 by an optical fiber or an electric cable passing through the inside of the slide pipe 26 and the arm 28.

FIGS. 3(A) and 3(B) show the swing mechanism 30 in detail. The swing mechanism 30 includes a pulse motor 40 provided at a forward end of the slide pipe 26, a bevel gear 42 fixed to a rotating shaft of the pulse motor 40, and a bevel gear 44 engaged with the bevel gear 42. The swing mechanism 30 further includes a small gear 46 provided coaxially with the bevel gear 44, a supporting shaft 48 rotatably supported on the slide pipe 26 and supporting the bevel gear 44 and the gear 46, a large gear 50 engaged with the small gear 46, and a swing shaft 52 rotatably supported on the slide pipe 26 and supporting the gear 50. Further, the pulse motor 40 is connected to a driver 54 (see FIG. 2) for controlling the pulse motor 40.

According to the inspecting apparatus 20 thus constructed, the image sensor 32 supported on the tip end of the arm 28 can be positioned in the vicinity of a roller-cutter 3 or an opening 4 by appropriately combining a front-rear motion and rotation of the slide pipe 26 and swing motion of the arm 28 driven by the pulse motor 40, thereby displaying the wear state of the roller-cutter 3 and the state of the ground or earth on the image display device 34. At this time, display spots by the image sensor 32 can be controlled while monitoring the image display device 34.

The above-mentioned inspection of a forward end portion in a tunnel boring machine is performed without workers entering into the chamber 7 and without discontinuing tunneling work or removing the excavated soil in the chamber 7.

Figure 4:
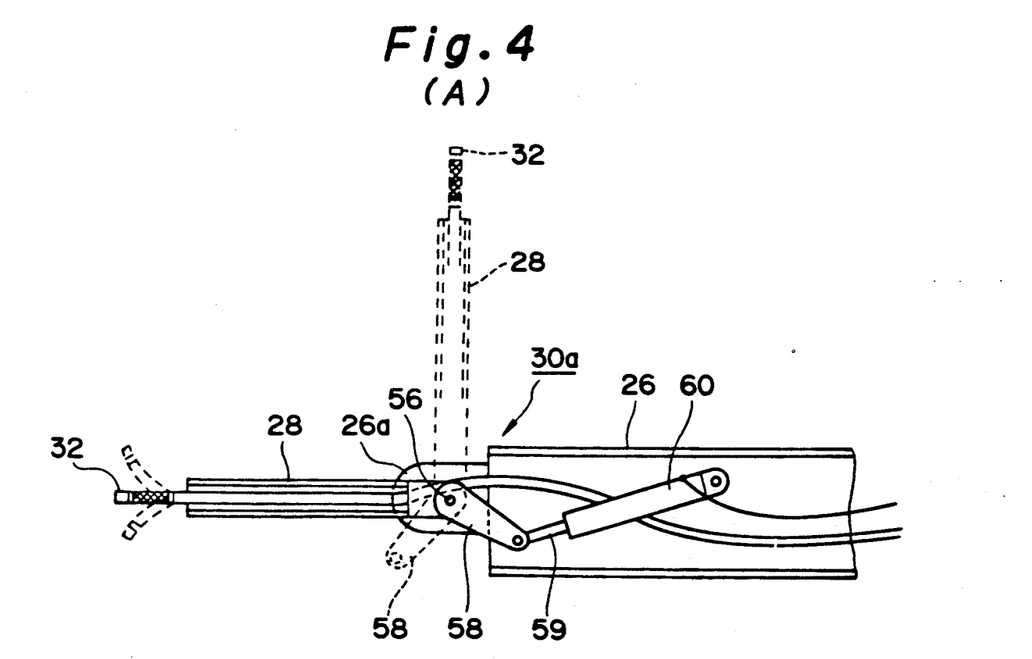
FIGS. 4(A) and 4(B) are cross-sectional views showing another swing mechanism in the apparatus for inspecting a forward end portion in a tunneling machine according to the first embodiment of the present invention.

FIGS. 4(A) and 4(B) show a modified embodiment of the swing mechanism of the arm 28.

A swing mechanism 30a is provided with a bearing member 26a provided on the tip end of the slide pipe 26 and a supporting shaft 56 is provided on the bearing member 26a. The arm 28 has a rear end which is supported by the supporting shaft 56. A pair of link arms 58 have one end which is connected to the supporting shaft 56 in such a manner that the arm 28 is sandwiched between the pair of link arms 58. Each of the link arms 58 has its other end connected to a plunger 59 of a jack 60. The jack 60 is swingably supported by a shaft provided at the forward end portion of the slide pipe 26.

According to the swing mechanism 30a thus constructed, when the jack 60 is actuated, the arm 28 is swung as shown by broken lines in FIG. 4(A). Therefore, inspection of a forward end portion in a tunnel boring machine can be performed in the same way as the first embodiment of the present invention.

In the first embodiment and the modified embodiment, the inspecting apparatus is applied to the tunnel boring machine. The inspecting apparatus according to the present invention is not limited to this type of tunneling machine, but, for example, is applicable to an earth pressure balance type or a slurry type of shield tunneling machine. In the shield tunneling type of machine, since the chamber is pressurized, for example, compressed air is introduced into the chamber prior to inspection to define a cavity in part, and the wear degree of the cutter bit at the forward end of the machine or the properties of the ground can be observed in the same way as the above embodiments.

As is apparent from the foregoing description, according to the inspecting apparatus of the first embodiment, since the wear state of the cutter bits and the properties of the ground can be observed and inspected without discontinuing the tunneling work of the tunneling machine, a lowering of the evacuation efficiency can be avoided.

Next, a second embodiment of an apparatus for inspecting a forward end portion in a tunneling machine will be described below with reference to FIGS. 5 through 9.

FIGS. 5(A)–(C) are schematic views showing a slurry type of shield tunneling machine to which an inspecting apparatus of the second embodiment is applied.

The shield tunneling machine includes a cylindrical main body 11 having both ends open, a cutter 12 rotatably provided at one open end of the main body 11, and a partition wall 14 secured to the main body 11 inside of the cutter 12 and at a predetermined distance from the cutter 12 as shown in FIG. 5(A). A chamber 16 is defined between the cutter 12 and the partition wall 14. A plurality of slit holes 12a (FIG. 5(C)) extending radially from the center are provided on the cutter 12 and a number of cutter bits 12b are fixedly provided at peripheral edges of each slit hole 12a.

A supply pipe 18 is connected to the upper portion of the partition wall 14 to supply the pressurized slurry to the chamber 16 and a discharge pipe 19 is connected to the lower portion of the partition wall 14 to discharge the excavated soil together with slurry to the outside.

Figure 5:
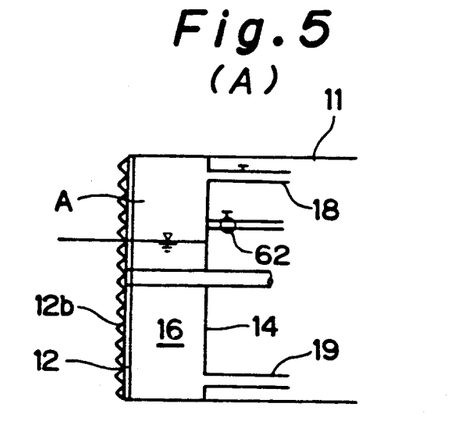
FIGS. 5(A), 5(B) and 5(C) are schematic explanatory views showing a shield tunneling machine to which an apparatus for inspecting a forward end portion in a tunneling machine according to a second embodiment of the present invention is applied.
Figure 6:
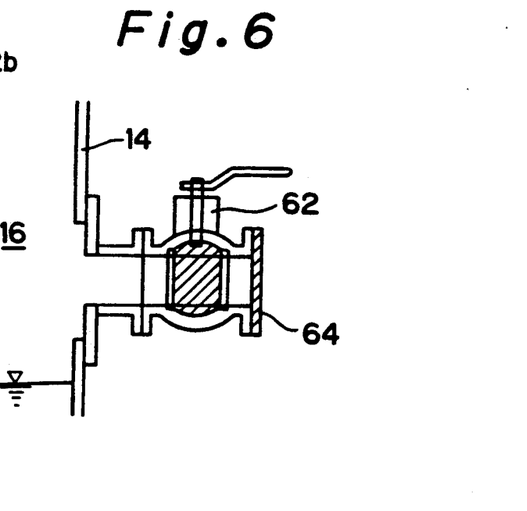
FIG. 6 is a cross-sectional view showing a valve for mounting the apparatus for inspecting a forward end portion in a tunneling machine according to the second embodiment of the present invention.
Figure 7:
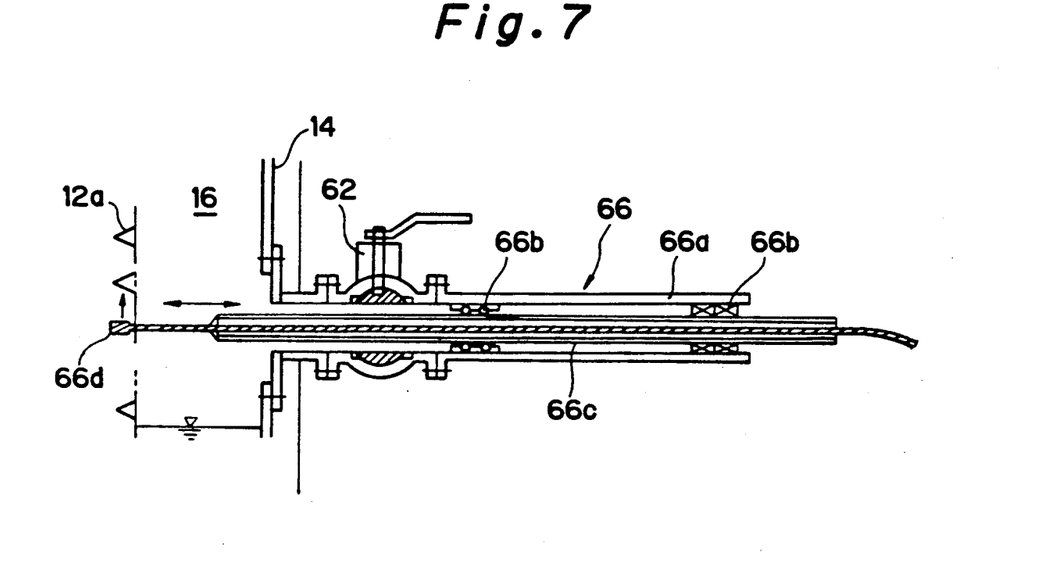
FIG. 7 is a cross-sectional view showing the apparatus for inspecting a forward end portion in a tunneling machine which is mounted on the valve of FIG. 6 according to the second embodiment of the present invention.

A valve 62 is attached to the partition wall 14 below the supply pipe 18 as shown in FIGS. 5(A) and 6. The valve 62 comprises a ball valve or a gate valve. In the normal condition, such as excavation, of the shield tunneling machine, the valve 62 is closed and a blanking cover 64 is attached to the one end of the valve 62. When observing and inspecting the inside of the chamber 16 or the cutter bits 12b of the cutter 12, an inspecting apparatus 66 is mounted on the valve 62 after removal of the blanking cover 64, as shown in FIG. 7.

The inspecting apparatus 66 comprises a seal pipe 66a having one end connected to a flange of the valve 62, a slide pipe 66c slidably provided in the seal pipe 66a through sealing members 66b in a water sealing or airtight state, and a fiber scope 66d constituting an image sensor provided in the slide pipe 66c so as to project the tip end thereof from the slide pipe 66c. The fiber scope 66d comprises an optical fiber. One end of the fiber scope 66d is connected to an image display device such as a TV monitor, an image analyzer or an illuminant device.

Next, a method for inspecting a forward end portion in a shield tunneling machine will be described below with reference to a flow chart in FIG. 8.

When observing and inspecting the inside of the chamber 56, first the shield tunneling machine is stopped for lowering the water level of muddy water to below the valve 62 (step 1).

In this case, compressed air is supplied to the chamber 16 by a compressed air supply device such as a compressor or a blower using the supply pipe 18 or another air supply pipe (not shown), thereby lowering the water level of muddy water up to a level necessary for observation and defining a partially cavity A having a higher pressure than the cutter face pressure (step 2).

Where a little ground water flows into the chamber 16 and the ground to be tunneled, and its surroundings are maintained to be stabilized, compressed air is not necessarily used to define the cavity A.

Incidentally, also in a slurry type of shield tunneling machine, the cavity A is defined by removing soil in the chamber in the same way as the above method.

After defining the cavity A, the blanking cover 64 is removed in a closed state of the valve 62 and the seal pipe 66a is mounted on the valve 62. Thereafter, the fiber scope 66d is inserted into the slide pipe 66c and the slide pipe 66c together with the fiber scope 66d is inserted into the seal pipe 66a (step 4, in this case step 3 is skipped).

After that, the slide pipe 66c is advanced in the open state of the valve 62 to position the tip end of the fiber scope 66d in the cavity A, and observation and inspection are performed in the chamber 16 by the inspecting apparatus 66 while moving the slide pipe 66c in a front-rear direction or rotating the slide pipe 66c (step 5).

Incidentally, if a water jet is ejected from a water supply tube or a water supply pipe to wash the tip end of the image sensor 66d or the observation spot and its surrounding area, or the cavity A is enlarged by washing the ground, it is possible to observe the observation spot more clearly.

After finishing observation, the slide pipe 66c is retracted to position the tip end of the slide pipe 66c rearward of the valve 62, and then the valve 62 is closed and the seal pipe 66a is removed from the valve 62. Thereafter, a countermeasure is studied as to how to cope with the situation on the basis of the observation results (step 6). In step 7, a countermeasure is taken to meet the situation, and the tunnel is again excavated (step 8). One of the countermeasures is for a worker to enter into the chamber 16.

When observing and inspecting the cutter bits 12b of the cutter 12, first the position of the valve 62 maybe almost aligned with a slit hole 12a for introducing soil on the cutter 12 (see FIGS. 5).

In this state, compressed air supplied to the chamber 16 to lower the water level of muddy water, thereby defining the cavity A around the cutter bits 12b. In order to ensure the defining of the cavity A, the shield tunneling machine is preferably retracted by a small distance while supplying compressed air to the cavity A.

After defining the cavity A, the cutter bits 12b of the cutter 12 are washed by a water jet (step 3). After step 3, the inspection is performed in accordance with steps 4 through 8 in FIG. 8 in the same way as that of the chamber 16. In step 7, one of the countermeasures is to replace the cutter bit with a new bit.

When observing the wear degree of the cutter bits 12b, each of the bits 12b provided corresponding to each of the slit holes 12a can be observed one after another by rotating the cutter 12.

Figure 8:
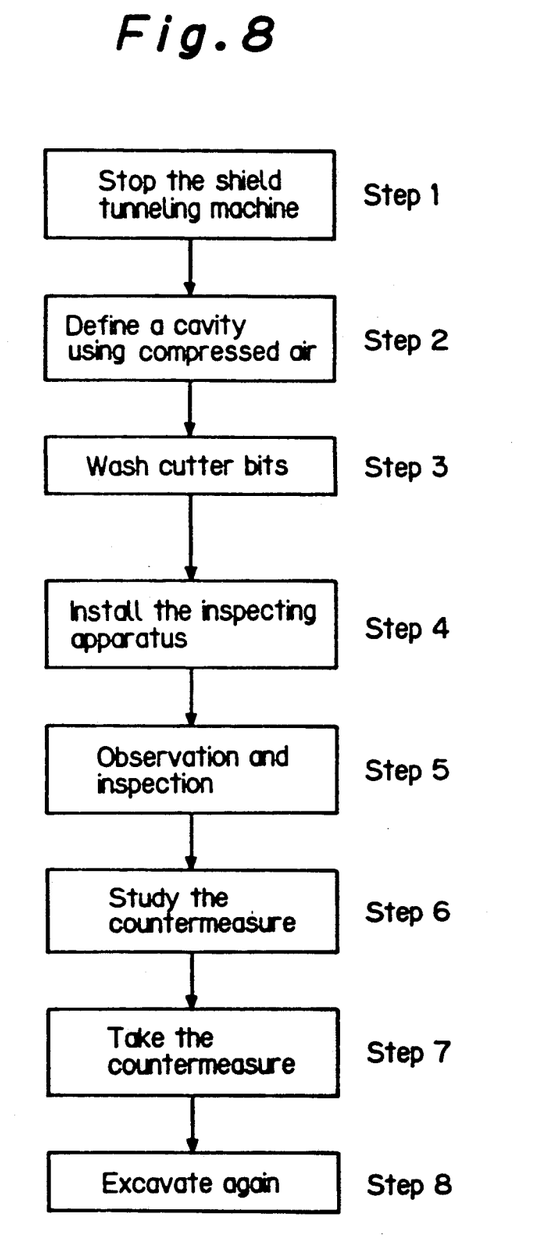
FIG. 8 is a flow chart showing a method for inspecting a forward end portion in a tunneling machine according to the present invention.
Figure 9:
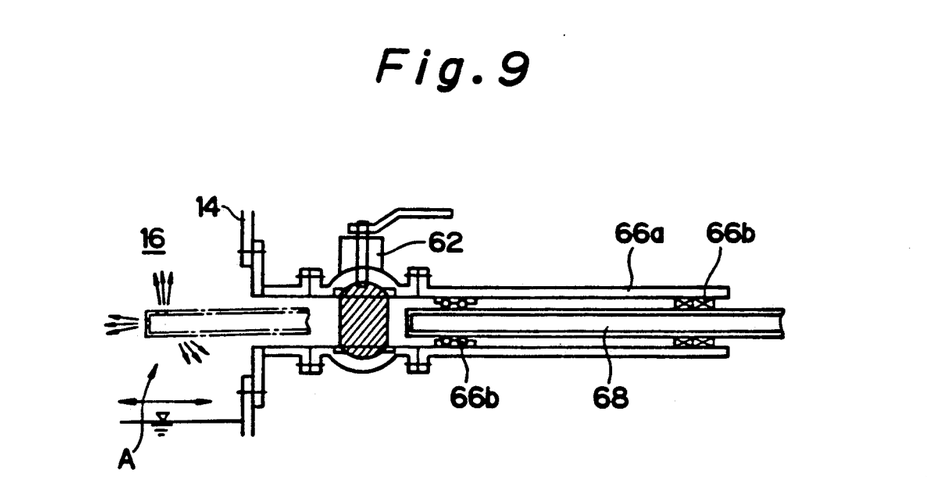
FIG. 9 is a cross-sectional view showing a washing process.

FIG. 9 shows the washing process of step 3 in FIG. 8. The washing of the inside of the chamber 56 or the cutter bit 12b is carried out prior to observation by the fiber scope 66d.

After defining the cavity A in the step 2, the seal pipe 66a is attached to the valve 62 and a water supply pipe 68 having the same diameter as the slide pipe 66c is slidably inserted into the seal pipe 66a in a water tight condition. The water supply pipe 68 is advanced toward the cavity A in the opened state of the valve 62, and then a water jet is ejected from the tip end of the water supply pipe 68 as shown in FIG. 9.

After washing the inside of the chamber 16 or the cutter bits 12b, the water supply pipe 68 is pulled out and the slide pipe 66c is inserted into the seal pipe 66a, and then the inside of the chamber 16 or the cutter bits 12b are observed and inspected by the fiber scope 66d.

In the case where the inside of the chamber 16 or the cutter bits are observed after washing them, the state of the chamber 16 or the wear state of the cutter bits 12b can be more exactly checked.

In the second embodiment, although only one valve 62 is attached to the partition wall 14, it should be noted that many changes and modifications may be made therein. For example, a plurality of valves 62 can be attached at suitable places, whereby a plurality of places may be observed by the fiber scope 66d.

Further, an opening or closing means for mounting the seal pipe 66a is not limited to the valve 62, but a shutter, for example, may be provided to open or shut between the seal pipe 66a and the chamber 16.

According to the second embodiment of the present invention, the observation spot of the image sensor can be widely changed by the front-rear motion and rotation of the slide pipe, therefore, the adhering or sticking to the inner chamber surfaces, the wear or the breakdown of the cutter bit, the properties of the ground or of the cutter face, or ground settlement can be exactly and reliably observed and inspected. When repair work is required on the basis of observation, the inspecting apparatus of the second embodiment can be utilized as a preliminary observation before a worker enters the chamber, or a confirmation monitor of work.

Next, a third embodiment of an apparatus for inspecting a forward end portion in a tunneling machine will be described below with reference to FIG. 10.

Figure 10:
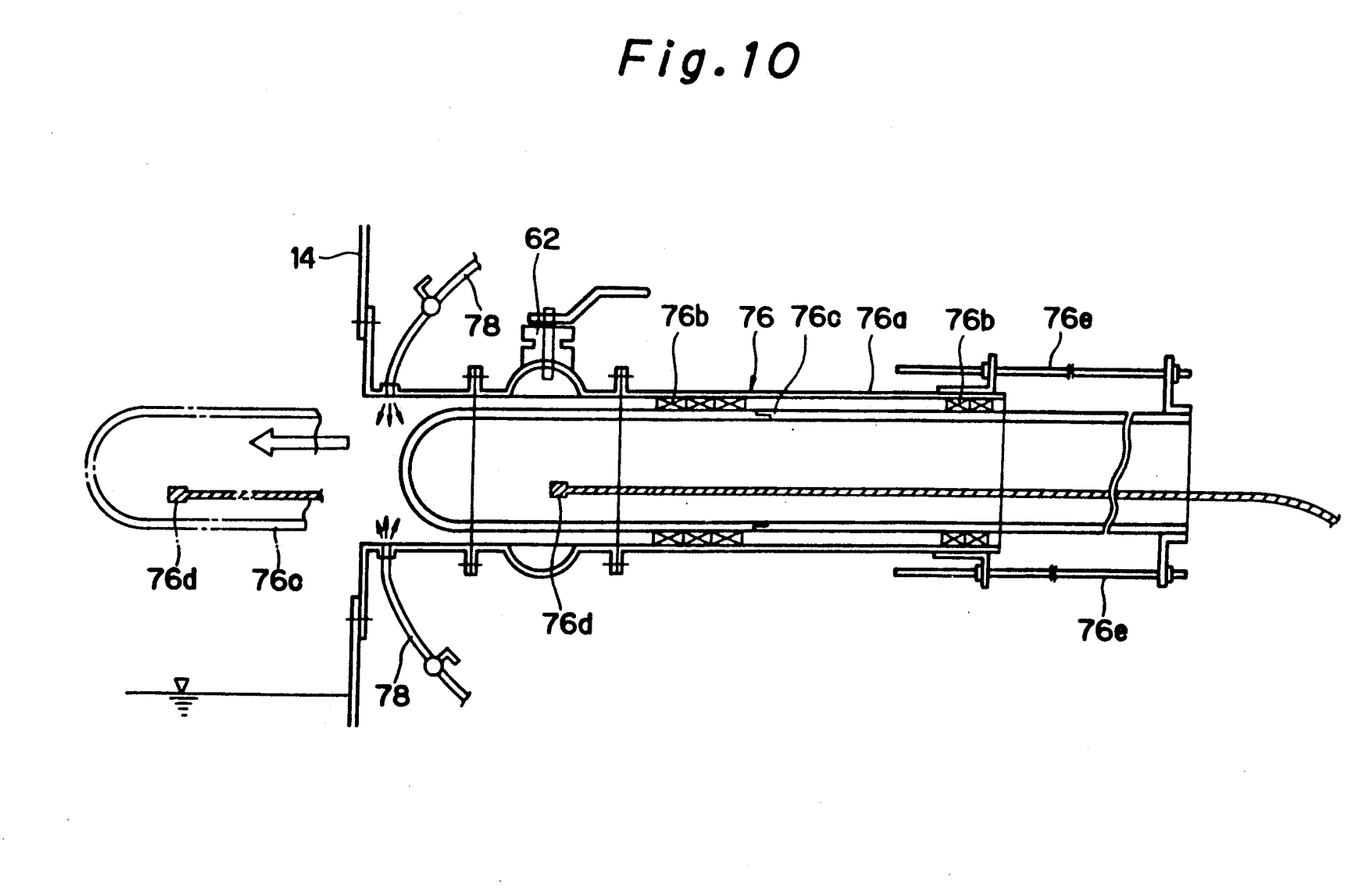
FIG. 10 is a cross-sectional view showing an apparatus for inspecting a forward end portion in a tunneling machine which is mounted on the valve of FIG. 6 according to a third embodiment of the present invention.

Those parts shown in FIG. 10 which are structurally and functionally identical to those shown in FIGS. 5 through 7 are denoted with identical reference numerals, and will not be described in detail.

In the third embodiment, the inspecting apparatus, 76 comprises a seal pipe 76a having one end connected to the flange of the valve 62, a pressure resisting pipe 76c slidably provided in the seal pipe 76a through sealing members 76b in a water sealing or airtight state, and a fiber scope 76d constituting an image sensor provided in the pressure resisting pipe 76c as shown in FIG. 10. The fiber scope 76d comprises an optical fiber, and one end of the fiber scope 76d is connected to an image display device such as a TV monitor, an image analyzer or an illuminant device.

The pressure resisting pipe 76c has an open rear end and a closed forward end, and at least the forward end portion is made of transparent pressure resisting glass to allow light to transmit therethrough.

Further, a plurality of guide rods 76e are provided at circumferentially spaced intervals between the rear end of the seal pipe 76a and the rear end of the pressure resisting pipe 76c.

On the other hand, water supply pipes 78 are provided on the valve 62 in the vicinity of the partition wall 14 to supply water jets to the pressure resisting pipe 76c and to wash it.

The method for inspecting a forward end portion using the inspecting apparatus 76 of the third embodiment is almost identical to that of the second embodiment except for attachment of the inspecting apparatus 76 to the valve 62 and the washing of the pressure resisting pipe 76c. That is, after defining the cavity A, the blanking cover 64 (see FIG. 6) is removed in a closed state of the valve 62 and the seal pipe 76a is mounted on the valve 62. Thereafter, the pressure resisting pipe 76c accommodating the fiber scope 76d is inserted into the seal pipe 76a while guiding the pressure resisting pipe 76c by the guide rods 76e. After that, the pressure resisting pipe 76c is advanced in an open state of the valve 62 to position the tip end of the fiber scope 76d in the cavity A, and observation and inspection are performed in the chamber 16 (see FIG. 5) by the inspecting apparatus 76 while moving the pressure resisting pipe 76c in a front-rear direction or rotating the same. At this time, preferably, a water jet is ejected toward the pressure resisting pipe 76c from the water supply pipes 78 to wash the transparent part of the pressure resisting pipe 76c. Other steps and effects of the third embodiment are identical to those of the second embodiment shown in FIG. 8.

A fourth embodiment of an apparatus for inspecting a forward end portion in a tunneling machine will be described below with reference to FIG. 11.

Figure 11:
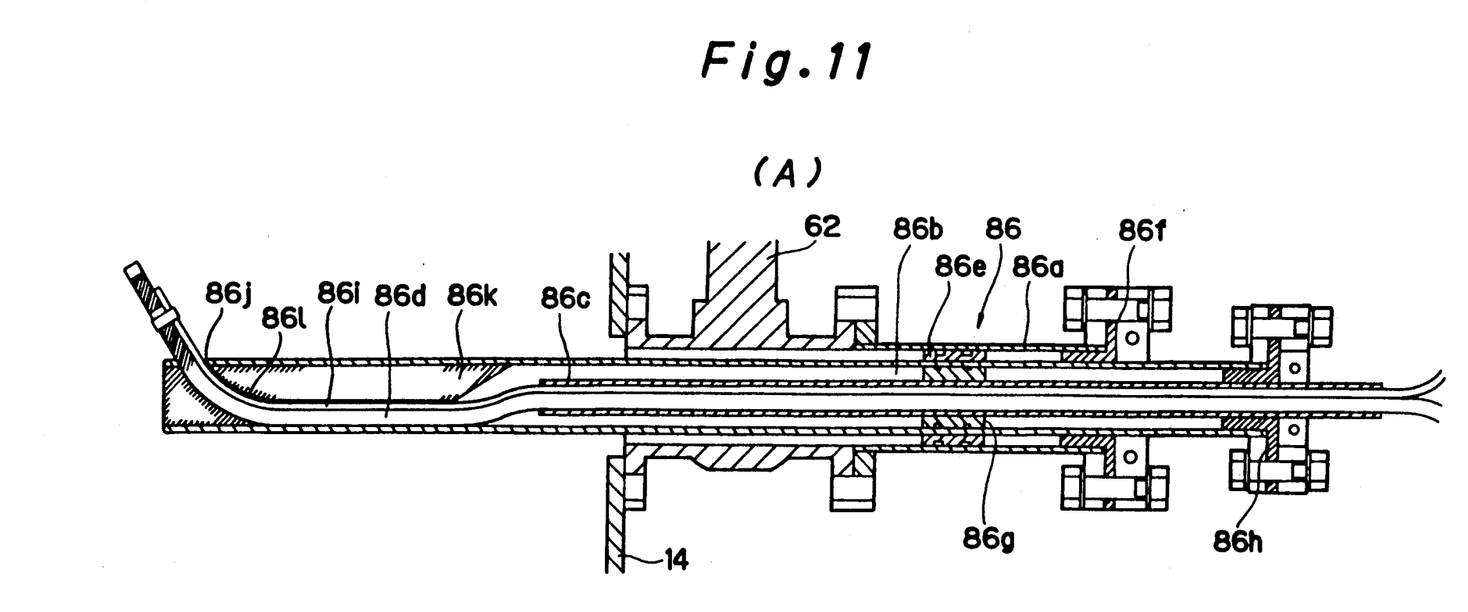
FIG. 11(A) is a cross-sectional view showing an apparatus for inspecting a forward end portion in a tunneling machine which is mounted on the valve of FIG. 6 according to a fourth embodiment of the present invention.
FIG. 11(B) is a partially enlarged cross-sectional view of FIG. 11(A)
FIG. 11(C) is an explanatory view showing an observation process using a fiber scope of FIGS. 11(A) and (B)

Those parts shown in FIG. 11 which are structurally and functionally identical to those shown in FIGS. 5 through 7 are denoted with identical reference numerals, and will not be described in detail.

In the fourth embodiment, the inspecting apparatus 86 comprises a seal pipe 86a having one end connected to the flange of the valve 62, a guide pipe 86b inserted into the seal pipe 86a, an inner guide pipe 86c provided in the guide pipe 86d, and a fiber scope 86b constituting an image sensor inserted into the inner guide pipe 86c. A seal member 86e with O rings and a supporting member 86f made of synthetic resin are interposed between the seal pipe 86a and the guide pipe 86b so that the guide pipe 86b is sealed in a water sealing or airtight state with respect to the seal pipe 86a and slidable in a front-rear direction and rotatable with respect to the seal pipe 86a.

Further, between the guide pipe 86b and the inner guide pipe 86c, there are provided a seal member 86g with an O ring and a spacer 86h so that the inner guide pipe 86c is sealed in a water sealing or airtight state with respect to the guide pipe 86b.

The fiber scope 86d constituting an image sensor comprises an optical fiber, and one end of the fiber scope 86d is connected to an image display device such as a TV monitor, an image analyzer or an illuminant device.

Further, a water supply tube 86i is provided along the fiber scope 86d to eject water therefrom.

A guide member 86k is provided at the forward end portion of the guide pipe 86b. The guide member 86k has a curved guide surface and the guide pipe 86b has a through hole 86j at the tip end portion thereof so that the fiber scope 86d is led in an oblique direction with respect to a longitudinal axis of the guide pipe 86b. The guide member 86k made of synthetic resin is formed with a through hole 86l which is curved smoothly and inclined at an angle of approximately 60° with respect to the longitudinal axis of the guide pipe 86b as shown in FIG. 11(b).

The method for inspecting a forward end portion using the inspecting apparatus 86 of the fourth embodiment is almost identical to that of the second embodiment except for the attachment of the inspecting apparatus 86 to the valve 62. To be more specific, after defining the cavity A, the blanking cover 64 (see FIG. 6) is removed in a closed state of the valve 62 and the seal pipe 86a is mounted on the valve 62. Thereafter, the fiber scope 86d is inserted into the inner guide pipe 86c and the guide pipe 86b together with the inner guide pipe 86c is inserted into the seal pipe 86a. After that, the guide pipe 86b is advanced in the open state of the valve 62 so as to project the fiber scope 86d from the through hole 86j in an oblique direction with respect to the longitudinal axis of the guide pipe 86b, thereby positioning the tip end of the fiber scope 86d in the cavity A and observing the inside of the chamber 16.

At this time, since the projecting length of the fiber scope 86d from the through hole 86j can be changed by advancing or retracting the inner guide pipe 86c relative to the guide pipe 86b as shown in FIG. 11(C), observations can be made at positions considerably spaced from the tip end of the guide pipe 86b, and observations can be also made on concentric circles having different radiuses from the central axis of the guide pipe 86b serving as the center of the radiuses. Therefore, it is possible to widely observe and inspect according to the inspecting apparatus 86 of the fourth embodiment.

Before observation, preferably, a water jet is ejected toward the tip end of the fiber scope 86d or the observation spot and its surrounding area.

On the other hand, in the fourth embodiment, observation of the cutter bits 12b (see FIG. 5) can be performed in the same way as with the third embodiment. At this time, in general, the cutter bits 12b positioned at an outer peripheral portion of the cutter 12 are worn away in its early stages. According to the inspecting apparatus 86 of the fourth embodiment, the projecting length of the fiber scope 86d from the through hole 86j can be changed, so that observation and inspection of the cutter bits 12b at the outer peripheral portion of the cutter 12 can be easily performed.

As is apparent from the foregoing description, according to the inspecting apparatus of the fourth embodiment, the observation spot of the image sensor can be widely changed by the front-rear motion and rotation of the guide pipe and alteration of the projecting length of the image sensor from the guide pipe. Therefore, the adhering or sticking to inner chamber surfaces, the wear or breakdown of the cutter bit, the properties of the ground or of the cutter face, or ground settlement can be exactly and reliably observed and inspected.

Figure 12:
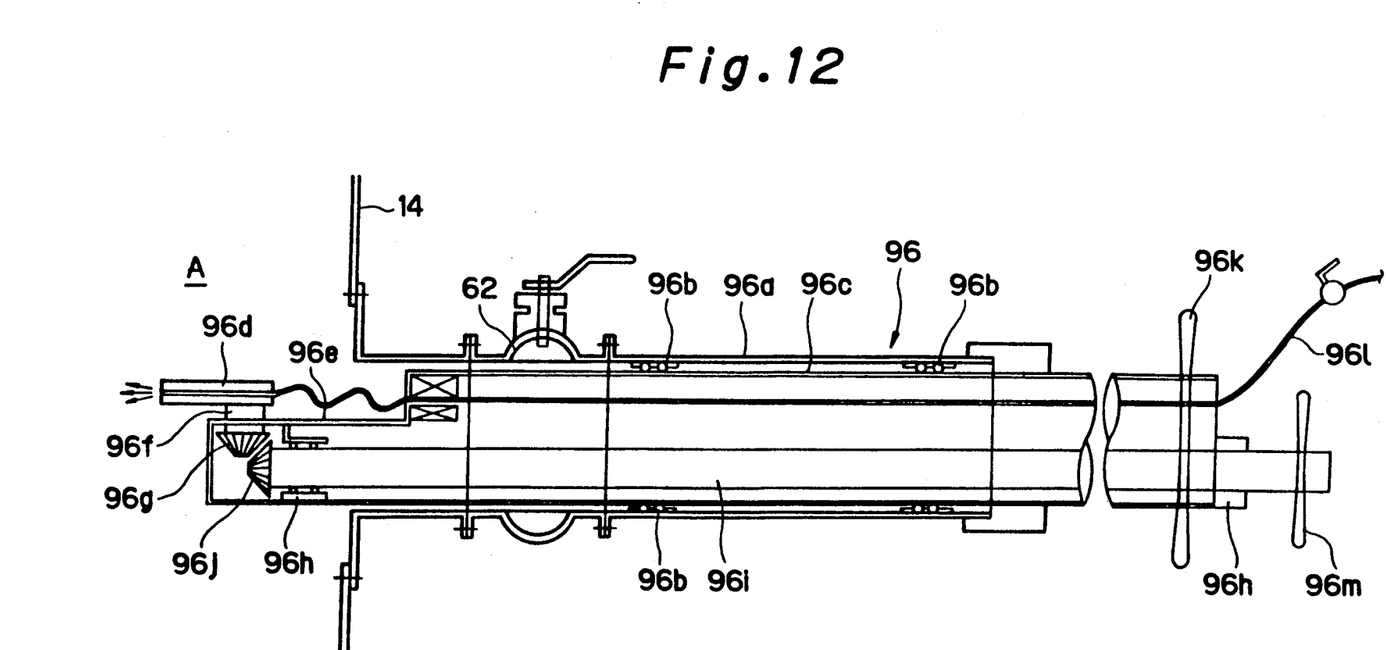
FIG. 12 is a cross-sectional view showing an apparatus for washing a forward end portion in a tunneling machine according to the present invention.

Next, a fifth embodiment of the present invention will be described below with reference to FIG. 12. This embodiment relates to an improvement on a washing apparatus.

A washing apparatus 96 comprises a seal pipe 96a having one end connected to the flange of the valve 62, a slide pipe 96c slidably provided in the seal pipe 96a through sealing members 96b in a water sealing or airtight state, and a nozzle 96d rotatably provided at the tip end of the slide pipe 96c. The slide pipe 96c has an open rear end and a closed forward end portion which has a step-like mounting portion 96e. A rotating shaft 96f is vertically provided on the mounting portion 96e so as to pierce through the mounting portion 96e. The nozzle 96d is fixedly secured to the upper end of the rotating shaft 96f, and a driven bevel gear 96g is fixed to the lower end of the rotating shaft 96f. A rotating rod 96i is rotatably provided in the slide pipe 96c through a rotating guide 96h fixed to the slide pipe 96c. A drive bevel gear 96j fixed to the forward end of the rotating rod 96i is engaged with the driven bevel gear 96g. A handle 96k and a handle 96m are fixedly attached to the respective rear ends of the slide pipe 96c and the rotating rod 96i. The nozzle 96d is connected to a water supply tube 96l provided in the slide pipe 96c.

Next, a mounting method and operation of the washing apparatus 96 will be described below.

When observing the inside of the chamber 16 (see FIG. 5), first the shield tunneling machine is stopped for lowering the water level of the muddy water to below the valve 62 (see FIG. 6).

In this case, compressed air is supplied to the chamber 16 from the supply pipe 18 (see FIG. 5), thereby defining a partial cavity A having a higher pressure than the cutter face pressure.

Incidentally, in the case where a little ground water flows into the chamber 16 and the ground to be tunneled and its surroundings can be stabilized, compressed air is not necessarily used to define the cavity A.

Alternatively, also in an earth pressure balance type of shield tunneling machine, the cavity A is defined by removing soil in the chamber in the same way as in the above method.

After defining the cavity A, the blanking cover 64 (see FIG. 6) is removed in a closed state of the valve 62 and the seal pipe 96a is mounted on the valve 62. Thereafter, the slide pipe 96c to which the nozzle 96d is attached is inserted into the seal pipe 96a, and the slide pipe 96c is advanced in the open state of the valve 62 to position the nozzle 96d in the cavity A. After that, a water jet is ejected while gradually moving the slide pipe 96c in the front-rear direction or rotating the same by operating the handle 96k, and simultaneously while rotating the rotating rod 96i to rotate the nozzle 96d by operating the handle 96m, thereby washing the inside of the chamber 16.

After finishing the wash, the slide pipe 96c is retracted so as to position the forward end of the nozzle 96d rearward of the valve 62, and then the valve 62 is closed and the slide pipe 96c is removed from the valve 62.

Thereafter, for example, the inspecting apparatus 76 as shown in FIG. 10 is attached to the valve 62, and observation and inspection are performed in the same way as with the third embodiment.

In the fifth embodiment, although only one valve 62 is attached to the partition wall 14, it should be noted that many changes and modifications may be made therein. For example, a plurality of valves 62 maybe attached to suitable places, whereby a plurality of places may be washed by the nozzle 96d.

Further in the embodiment, the rotating rod 96i is illustrated in conjunction with the bevel gears 96g and 96j as a rotating mechanism of the nozzle 96d. However, the nozzle 96d maybe directly rotated by an electric motor or an oil hydraulic motor instead of the above rotating mechaism.

According to the washing apparatus of the fifth embodiment of the present invention, a washing position of the nozzle can be widely changed by moving the slide pipe in a front-rear direction and rotating the same. Therefore, the adhering or sticking to inner chamber surfaces, the wear or breakdown of the cutter bit, the property of the ground or of the cutter face, or the ground settlement can be exactly and reliably observed and inspected.

Although certain preferred embodiment have been shown and described, it should be understood that many changes and modifications may be made therein without departing from the scope of the appended claims.

What is claimed is:

1. An apparatus for inspecting a forward end portion in a tunneling machine including a main body, a cutter member rotatably provided at a forward end portion of the main body and having a plurality of cutter bits and openings thereon, and a partition wall provided inside of the cutter member to define a chamber between the cutter member and the partition wall, the apparatus comprising:
   at least one through hole provided in said partition wall;
   an elongate member inserted into said through hole, said elongate member being slidable in a front-rear direction and rotatable around its longitudinal axis;
   an image sensor positioned at a forward end of said elongate member;
   image displaying means provided in said main body for displaying an image from said image sensor; and
   connecting means for connecting said image sensor and said image displaying means, said connecting means extending in said elongate member.

2. The apparatus for inspecting a forward end portion in a tunneling machine as claimed in claim 1, and further comprising means for closing or opening said through hole and means for sealing a clearance between said elongate member and said through hole.

3. The apparatus for inspecting a forward end portion in a tunneling machine as claimed in claim 1, and further comprising an arm provided at the forward end of said elongate member for supporting said image sensor and a swing mechanism provided between said arm and said elongate member for swinging said arm.

4. The apparatus for inspecting a forward end portion in a tunneling machine as claimed in claim 3, wherein said swing mechanism comprises a gear train and a motor for driving said gear train.

5. The apparatus for inspecting a forward end portion in a tunneling machine as claimed in claim 3, wherein said swing mechanism comprises a linkage and an actuator for actuating said linkage.

6. The apparatus for inspecting a forward end portion in a tunneling machine as claimed in claim 1, wherein said image sensor comprises one of a fiber scope and a charge coupled device.

7. The apparatus for inspecting a forward end portion in a tunneling machine as claimed in claim 1, wherein said elongate member comprises a hollow pipe and said image sensor comprises a fiber scope whose tip end projects from the tip end of said hollow pipe.

8. The apparatus for inspecting a forward end portion in a tunneling machine as claimed in claim 1, wherein said connecting means comprises an electric cable.

9. The apparatus for inspecting a forward end portion in a tunneling machine as claimed in claim 1, wherein said connecting means comprises an optical fiber.

10. The apparatus for inspecting a forward end portion in a tunneling machine as claimed in claim 1, wherein said elongate member comprises a hollow pipe having a closed forward end made of transparent material and said image sensor is disposed inside of said forward end of said hollow pipe.

11. The apparatus for inspecting a forward end portion in a tunneling machine as claimed in claim 10, and further comprising a water supply tube for washing said forward end of said elongate member.

12. The apparatus for inspecting a forward end portion in a tunneling machine as claimed in claim 1, and further comprising a hollow pipe accommodated in said elongate member and a guide member provided at a forward end portion of said elongate member, wherein said image sensor comprises a fiber scope inserted into said inner pipe, said fiber scope pierces through a side wall of said elongate member at a forward end portion thereof and is guided in an oblique direction with respect to a longitudinal axis of said elongate member.

13. The apparatus for inspecting a forward end portion in a tunneling machine as claimed in claim 12, wherein said fiber scope projects from said side wall of said elongate member, the projecting length of said fiber scope being variable.

14. A method for inspecting a forward end portion in a tunneling machine including a main body, a cutter member rotatably provided at a forward end portion of the main body and having a plurality of cutter bits and openings thereon, and a partition wall provided inside of the cutter member to define a chamber between the cutter member and the partition wall, the method comprising the steps of:

defining a cavity in said chamber or in the vicinity of said cutter bits by supplying compressed air;
inserting an image sensor into said cavity, said image sensor piercing through said partition wall and being sealed relative to said partition wall; and
observing the inside of said chamber or said cutter bits using said image sensor.

15. The method for inspecting a forward end portion in a tunneling machine as claimed in claim 14, and further comprising the step of washing the inside of said chamber or said cutter bits.

16. An apparatus for washing a forward end portion in a tunneling machine including a main body, a cutter member rotatably provided at a forward end portion of the main body and having a plurality of cutter bits and openings thereon, and a partition wall provided in the main body to define a chamber between the cutter member and the partition wall, the apparatus comprising:

at least one through hole formed in said partition wall;
an elongate member extending in said main body and into said chamber through said through hole, said elongate member being rotatable around a longitudinal axis thereof and slidable in an axial direction of said main body;
a nozzle mounted on a forward end portion of said elongate member, said nozzle being rotated around the longitudinal axis of said elongate member by a rotational movement of said elongate member, and said nozzle having a shaft extending in a direction substantially perpendicular to the longitudinal axis of said elongate member;
revolving means provided in said elongate member for revolving said shaft around its axis to thereby turn said nozzle around said shaft; and
a water supply tube extending in said elongate member for supplying water to said nozzle.

17. The apparatus for washing a forward end portion in a tunneling machine of claim 16, wherein said revolving means comprises a rotatable rod connected to said shaft by a gear mechanism.

18. The apparatus for washing a forward end portion in a tunneling machine of claim 16, wherein said forward end portion of said elongate member has a recessed step mounting portion rotatably mounting said shaft.

* * * * *